United States Patent [19]

Baragi et al.

[11] Patent Number: 5,703,119
[45] Date of Patent: Dec. 30, 1997

[54] BENZYLIDENE-LACTONE DERIVATIVES OF FENAMATES AND THEIR THIOCARBONYL ANALOGS AS INHIBITORS OF PROTEOGLYCAN DEGRADATION

[75] Inventors: Vijaykumar Baragi, Ann Arbor; Diane Harris Boschelli, Plymouth; David Thomas Connor, Ann Arbor; Richard Raymond Renkiewicz, Novi, all of Mich.

[73] Assignee: Warner-Lambert Company, Morris Plains, N.J.

[21] Appl. No.: 448,817

[22] Filed: May 24, 1995

Related U.S. Application Data

[62] Division of Ser. No. 273,668, Jul. 12, 1994, abandoned, which is a division of Ser. No. 97,356, Jul. 26, 1993, Pat. No. 5,358,964.

[51] Int. Cl.[6] .................... C07D 309/30; A61K 31/35
[52] U.S. Cl. .................... 514/459; 549/293; 549/416
[58] Field of Search .................... 549/416, 293; 514/459

[56] References Cited

U.S. PATENT DOCUMENTS

| 4,431,656 | 2/1984 | Katsumi et al. | 549/389 |
| 5,217,709 | 6/1993 | Lagrange et al. | 424/47 |

FOREIGN PATENT DOCUMENTS 0204964  12/1986  European Pat. Off. .

*Primary Examiner*—Jane Fan

[57] ABSTRACT

The manufacture and use of compounds of the formula

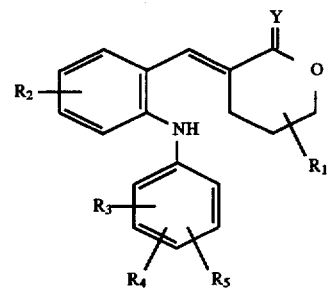

wherein Y is O or S, $R_1$ is hydrogen or alkyl, and $R_2$, $R_3$, $R_4$ and $R_5$ are hydrogen or various substituent groups, and pharmaceutically acceptable acid addition salts thereof. The compounds have activity as inhibitors of the IL-I or other agonist-induced proteoglycan degradation in bovine nasal cartilage and pharmaceutical compositions containing such compounds are described to treat conditions advantageously affected by such inhibition including arthritis.

7 Claims, No Drawings

BENZYLIDENE-LACTONE DERIVATIVES OF FENAMATES AND THEIR THIOCARBONYL ANALOGS AS INHIBITORS OF PROTEOGLYCAN DEGRADATION

This is a divisional of U.S. application Ser. No. 08/273,668 filed Jul. 12, 1994, now abandoned, which is a divisional of U.S. application Ser. No. 08/097,356 filed Jul. 26, 1993, now U.S. Pat. No. 5,358,964.

BACKGROUND OF THE INVENTION

The present invention relates to novel compounds which are 2-substituted α-benzylidene-γ-butyrolactone, α-benzylidene-δ-valerolactone, α-benzylidene-γ-butyrolactam, and α-benzylidene-δ-valerolactam derivatives of the fenamic acids. The invention compounds have activity as inhibitors of the IL-1-induced proteoglycan (PG) degradation in bovine nasal cartilage providing treatment of conditions advantageously affected by such inhibition including arthritis, and the like. IL-1 is one example of an agonist causing PG degradation. Other agonists including TNF and PMA also cause PG degradation. The compounds of the present invention block PG degradation caused by various agonists, and the description of inhibition of IL-1 induced PG degradation is illustrative rather than exclusive.

Although fenamates are known antiinflammatory agents and various substituted α-benzylidene-γ-butyrolactone and α-benzylidene-γ-butyrolactam derivatives are known as useful substituents in derivations of 3,5-di-tertiary-butyl-4-hydroxyphenyl groups as disclosed in U.S. Pat. No. 4,431,656 and in European Patent Publication 0204964, the present combination of ring systems, substituents, and moieties is not among those previously known.

SUMMARY OF THE INVENTION

Accordingly, the present invention is first a compound of Formula I

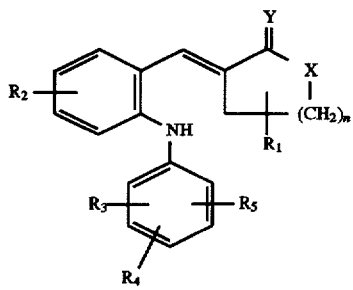

wherein
X is O or N—OCH$_3$;
Y is O or S;
R$_1$ is hydrogen or lower alkyl;
n is an integer of 1 or 2; and
R$_2$, R$_3$, R$_4$, and R$_5$ are each independently hydrogen, halogen, trifluoromethyl, lower alkyl, CN, hydroxy, lower alkoxy, S(O)$_m$-lower alkyl, NO$_2$, or NR$_6$R$_7$ wherein R$_6$ and R$_7$ are each independently hydrogen, lower alkyl, lower alkanoyl or benzoyl, and m is an integer of 0, 1, or 2, or a pharmaceutically acceptable acid addition salt thereof.

The present invention in a second aspect includes a pharmaceutical composition for the treatment of a condition advantageously affected by the inhibition of IL-1 and other agonist induced proteoglycan degradation which comprises an amount effective for the treatment of the condition of a compound of the Formula I or a pharmaceutically acceptable acid addition salt thereof, together with a pharmaceutically acceptable carrier. The "condition" is meant to include arthritis, e.g., rheumatoid arthritis and osteoarthritis, cancer, periodontitis, and osteoporosis.

The present invention in a third aspect includes a method for treatment of the condition as noted above in mammals, including humans, suffering therefrom with a compound of the Formula I or a pharmaceutically acceptable acid addition salt thereof in unit dosage form. Particularly, the present invention includes a method for treatment of arthritis in a mammal suffering therefrom which comprises administration to said mammal a pharmaceutical composition as described above or a compound of the Formula I in unit dosage form.

Pharmaceutical composition or use of the compound or salt of Formula I is meant to include treatment understood to be prophylactic pertinent to the foregoing named condition.

DETAILED DESCRIPTION OF THE INVENTION

In the compounds of Formula I, the term "lower alkyl" and in general the term "lower" used before alkoxy and alkanoyl includes a hydrocarbon radical of from 1 to 6 carbon atoms such as methyl, ethyl, propyl, butyl, and the like, as well as branched isomers thereof.

Halogen is meant to include fluoro, chloro, bromo, or iodo.

"Alkoxy" is limited to "lower" as defined above and includes, for example, methoxy, ethoxy, propoxy, butoxy, and the like, as well as branched isomers thereof.

"Alkanoyl" is a carbonyl group more commonly known as acyl having from 2 to 6 carbon atoms by the "lower" limitation defined above and includes, for example, acetyl, propionyl, butyryl, and the like, and branched isomers thereof.

Me stands for methyl.

Pharmaceutically acceptable acid addition salts within the scope of the invention may be those derived from mineral acids such as hydrochloric acid and sulfuric acid; and organic acids such as ethanesulfonic acid, benzenesulfonic acid, p-toluenesulfonic acid, and the like, giving the hydrochloride, sulfate, ethane-sulfonate, benzenesulfonate, p-toluenesulfonate, and the like, respectively.

The acid addition salts are prepared by dissolving the free base of Compound I in aqueous or aqueous alcohol solution or other suitable solvents containing the appropriate acid and isolating the salt by evaporating the solution, or by reacting the free base of Compound I with an acid such that the reactions are in an organic solvent, in which case the salt separates directly or can be obtained by concentration of the solution. Salts can also be prepared by adding base to an aqueous alcohol solution of another salt.

The compounds of the invention are geometric isomers of the "E" configuration.

In determining when an IL-1-induced proteoglycan degradation inhibitor is indicated, of course inter alia, the particular condition in question and its severity, as well as the age, sex, weight, and the like of the subject to be treated, must be taken into consideration and this determination is within the skill of the attendant physician.

For medical use, the amount required of a compound of Formula I or pharmacologically acceptable salt thereof to achieve a therapeutic effect will, of course, vary both with the particular compound, the route of administration, the mammal under treatment, and the particular disorder or disease concerned. A suitable dose of a compound of Formula I or pharmacologically acceptable salt thereof for a mammal suffering from, or likely to suffer from any condition as described hereinbefore, is 0.1 µg to 500 mg of the compound per kilogram body weight per day. In the case of systemic administration, the dose may be in the range of 0.5 to 500 mg of the compound per kilogram body weight, the most preferred dosage being 0.5 to 50 mg/kg of mammal body weight administered two or three times daily. In the case of topical administration, e.g., to the skin or eye, a suitable dose may be in the range 0.1 ng to 100 µg of the compound per kilogram, typically about 0.1 µg/kg.

In the case of oral dosing for the treatment or prophylaxis of arthritis or inflammation in general, due to any course, a suitable dose of a compound of Formula I or physiologically acceptable salt thereof, may be as specified in the preceding paragraph, but most preferably is from i mg to 10 mg of the compound per kilogram, the most preferred dosage being from 1 mg to 5 mg/kg of mammal body weight, for example from 1 to 2 mg/kg.

It is understood that the ordinarily skilled physician or veterinarian will readily determine and prescribe the effective amount of the compound to prevent or arrest the progress of the condition for which treatment is administered. In so proceeding, the physician or veterinarian could employ relatively low doses at first, subsequently increasing the dose until a maximum response is obtained.

While it is possible for an active ingredient to be administered alone, it is preferable to present it as a pharmaceutical formulation comprising a compound of Formula I or a pharmacologically acceptable acid addition thereof and a pharmacologically acceptable carrier therefor. Such formulations constitute a further feature of the present invention.

The formulations, both for veterinarian and for human medical use, of the present invention comprise an active ingredient in association with a pharmaceutically acceptable carrier therefor and optionally other therapeutic ingredient(s). The carrier(s) must be 'acceptable' in the sense of being compatible with the other ingredients of the formulations and not deleterious to the recipient thereof.

The formulations include those in a form suitable for oral, pulmonary, ophthalmic, rectal, parenteral (including subcutaneous, intramuscular, and intravenous), intraarticular, topical, nasal, or buccal administration. Such formulations are understood to include long-acting formulations known in the art.

The formulations may conveniently be presented in unit dosage formand may be prepared by any of the methods well-known in the art of pharmacy. All methods may include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units such as capsules, cachets, tablets, or lozenges, each containing a predetermined amount of the active ingredient; in the form of a powder or granules; in the form of a solution or a suspension in an aqueous liquid or nonaqueous liquid; or in the form of an oil-in-water emulsion or a water-in-oil emulsion. The active ingredient may also be in the form of a bolus, electuary, or paste.

The usefulness of the compounds of the present invention as inhibitors of IL-1-induced proteoglycan degradation, or in treating related diseases or conditions may be demonstrated by their effectiveness in the following test procedure.

Interleukin-1 has been shown to induce a loss of proteoglycans from cartilage cultures, possibly by stimulating synthesis of the proteoglycan degrading enzyme stromelysin. The BNC (bovine nasal cartilage) assay provides a model for evaluating chrondroprotective compounds that block cartilage degradation through inhibition of enzyme activity or by altering the gene expression of the matrix metalloproteinase stromelysin.

Matrix metalloproteinases (MMPs), including stromelysin are important enzymes for the degradation of extracellular matrix components such as collagen and proteoglycans in many disease processes including rheumatoid arthritis, osteoarthritis, cancer, periodontitis, and osteoporosis. MMPs are also involved in eye diseases such as corneal ulcer formation.

Materials

Bovine nasal cartilage is obtained from a local slaughter house (Milan, Mich.); cell culture reagents from Gibco (Grand Island, N.Y.); human recombinant Interleukin-1β (IL-1β) from Boehringer Mannheim (Indianapolis, Ind.); DMB from Polysciences (Warrington, Pa.); Falcon 24 well flat-bottom tissue culture plates from Becton Dickinson (Lincoln Park, N.J.); disposable 20-mL scintillation vials from Kimble Glass (Vinland, N.J.); Papain from Sigma (P-3125, St. Louis, Mo.); high purity dimethyl sulfoxide from Burdic & Jackson (081-1, Distributed by Baxter Healthcare, McGraw Park, Ill.); Sarstedt vials for radioimmune assays (Sarstedt, Newton, N.C.); Sarstedt 96-vial aluminum racks (Sarstedt, Newton, N.C.); Cetus Pro/Pette (Perkin Elmer, Norwalk, Conn.).

Methods

The assay is accomplished in two phases. The cartilage plugs are first incubated with IL-1 in the presence of compounds. The amount of proteoglycan released is then quantified by measuring chondroitin sulfate present in the media using the 1,9-Dimethyl-methylene Blue Assay.

Cartilage Culture. Bovine nasal septum is dissected free of surrounding tissue and wiped with 70% alcohol. A sterile cork borer is used to remove 5-mm cartilage disks of 2 to 3 mm thickness. Explants are equilibrated for 96 hours in F-12 supplemented with 10% fetal calf serum (FCS) and antibiotics at 37° C. in a humidified atmosphere of 95% air and 5% $CO_2$. Explants are then rinsed with 1 mL F-12 Nutrient Mixture (without phenol red) in order to remove traces of FCS. Each treatment group is done in triplicate allowing: controls (500 µL F-12 medium+110 µL PBS with 0.1% BSA+7 µL DMSO); IL-1β (500 µL F-12 medium without phenol red+100 µL IL-1β (500 U)+7 µL DMSO+10 µL PBS with 0.1% BSA); and dose responses (10, 1, and 0.1 µM) (F-12 medium without phenol red+100 µL IL-1β (500 U)+7 µL compound dissolved in DMSO+10 µL PBS with 0.1% BSA), to be tested per each 24-well plate. The cartilage plugs are incubated in the presence of conditioned media (IL-1β+compound) for 48 hours. Fresh unconditioned media (no IL-1β or compound) is added and incubated for an additional 24 hours. Both the conditioned and unconditioned media is collected and saved for analysis using the 1,9 DMB assay.

Quantitation of Cartilage Degradation. The ability of a compound to inhibit proteoglycan released from the cartilage plugs is quantified by measuring chondroitin sulfate. This is done using the colorimetric 1,9 DMB assay. Depending on the amount of chondroitin sulfate present in the media a color change will occur turning the normally deep blue dye, vivid pink. This color change is measured using a Titertek Multiscan MCC 340 plate reader at 540 nm. A Cetus Pro/Pette is used to speed dilution and pipetting steps. The Cetus uses Sarstedt vials, designed for radioimmune assays, which have been inserted into Sarstedt 96-vial aluminum racks. The first row of 12 slots is left empty in order to accommodate the chondroitin sulfate standards (0.01–0.32 µg/mL shark chondroitin sulfate in 0.1M phosphate buffer, pH 7.0, containing 0.01M L-cysteine HCl and 0.05M EDTA). It is necessary to dilute (1:5, 1:10) the medium before a DMF assay is performed by adding 10 µL of collected media to 290 µL DMF (16 mg dye/1 L of 0.1M formate buffer, pH 3.5, containing 5 mL ethanol) and reading 540 nM. Dilutions are performed on both the 48-hour and 72-hour media samples collected and saved earlier. Once the experiment has been completed in order to determine the total amount of proteoglycan remaining in the plugs they are subjected to papain digestion. Cartilage explants are digested in 20-mL glass scintillation vials by adding 50 µL papain in 1.0 mL cysteine buffer (0.01M phosphate buffer, pH 7.0 containing 0.01M L-cysteine HCl and 0.05 M EDTA). Digested material is diluted (1:60) and chondroitin sulfate values determined using the 1,9 DMB assay.

Data Acquisition and Analysis

Absorbance readings from the multi-well plate reader were transferred via the RS232 port to an IBM Personal System/2 Model 60 computer and captured using Lotus Measure (Lotus Development Corporation, Cambridge, Mass.). All statistical analysis of the data is done using Lotus 1-2-3 (Lotus Development Corporation, Cambridge, Mass.).

Determinations of chondroitin sulfate in each sample is accomplished by subtracting the constant value determined from the linear regression performed on the standard curve, from the O.D. value for a particular well and then dividing by the X coefficient calculated from the linear regression done on the standard curve. Each experimental well is split into two samples for determining chondroitin sulfate values, then the two are averaged. This averaged number is multiplied by the total volume, 617 or 500 depending on the time point being assayed, divided by the volume being assayed (10 µL), and multiplied by the dilution factor (1, 5, 10) to give a total amount of chondroitin sulfate present per experimental well. Once a total value has been determined for each dilution the numbers are compared to find the highest total chondroitin sulfate values ensuring that you have real numbers which are falling on the standard curve. The highest chondroitin sulfate values are transferred to a summary sheet for both the 48-hour and 72-hour media samples. Total chondroitin sulfate present in the cartilage plug after papain digestion is then determined. A 1:60 dilution is generally effective in getting the absorbance readings within the standard curve. Once chondroitin sulfate values have been determined for the plugs they also are transferred to the summary sheet. At this time summary sheet input is complete and release values, as well as inhibition (%), can be calculated. Release is calculated using the formula: (48-hour media+72-hour media)/(48-hour media+72-hour media+digest). Percent inhibition is calculated using the following formula: (((Treatment Release-Control)/(IL-1 Release Control)) *100).

The following table-reports the inhibition activity of representative compounds of Formula I.

| Inhibition Activity in Bovine Nasal Cartilage Assay | |
|---|---|
| Compound Example Number | $IC_{50}$ (µM) or Percent Inhibition @ µM |
| 1 | 0.39 |
| 2 | >50% @ 10.0 |
| 3 | 0.52 |
| 4 | 70% @ 0.10 |

Accordingly, the present invention is for a compound of the Formula I or pharmaceutically acceptable salt thereof, and a pharmaceutical composition or method of use in treating conditions advantageously effected by inhibiting IL-1 and other agonists induced proteoglycan degradation such as outlined above.

Preferred compounds of Formula I are those wherein $R_1$ is hydrogen, methyl, or ethyl.

Particularly valuable are:

(E)-3-[[2-[(2,6-dichloro-3-methylphenyl)amino]-phenyl]methylene]-4,5-dihydro-2(3H)-furanone, (E)-3-[[2-[(2,6-dichloro-3-methylphenyl)amino]-phenyl]methylene]-4,5-dihydro-2(3H)-furanthione, (E)-4,5-dihydro-3-[[2-[3-(trifluoromethyl)phenyl]-amino]phenyl]methylene]-2(3H )-furanone, and (E)-4,5-dihydro-3-[[2-(phenylamino)phenyl]-methylene]-2(3H)-furanone or a pharmaceutically acceptable acid addition salt thereof.

In addition to the compounds of Formula I, the pharmaceutical compositions can also contain other active ingredients, such as nonsteroidal antiinflammatory drugs (NSAIDS). The weight ratio of the compound of the Formula I to the second active ingredient may be varied and will depend upon the effective dose of each ingredient. Generally, an effective dose of each will be used. Thus, for example, when a compound of the Formula I is combined with an NSAID, the weight ratio of the compound of the Formula I to the NSAID will generally range from about 1000:1 to about 1:1000, preferably about 200:1 to about 1:200.

NSAIDS can be characterized into five groups:

(1) the propionic acid derivatives;
(2) the acetic acid derivatives;
(3) the fenamic acid derivatives;
(4) the biphenylcarboxylic acid derivatives; and
(5) the oxicams or a pharmaceutically acceptable salt thereof.

The propionic acid derivatives which may be used comprise: ibuprofen, ibuprofen aluminum, indoprofen, ketoprofen, naproxen, benoxaprofen, flurbiprofen, fenoprofen, fenbufen, pirprofen, carprofen, oxaprozin, pranoprofen, microprofen, tioxaprofen, suprofen, alminoprofen, tiaprofen, fluprofen, and bucloxic acid. Structurally related propionic acid derivatives having similar analgesic and antiinflammatory properties are also intended to be included in this group.

Thus, "propionic acid derivatives" as defined herein are nonnarcotic analgesics/nonsteroidal antiinflammatory drugs having a free —$CH(CH_3)COOH$ or —$CH_2CH_2COOH$ group (which optionally can be in the form of a pharmaceutically acceptable salt group, e.g., —$CH(CH_3)COO^-Na^+$ or —$CH_2(CH_2)COO^-Na^+$), typically attached directly or via a carbonyl function to a ring system, preferably to an aromatic ring system.

The acetic acid derivatives which may be used comprise: indomethacin, which is a preferred NSAID, sulindac, rolmerin, zomepirac, diclofenac, fenclofenac, alclofenac, ibufenac, isoxepac, furofenac, tiopinac, zidometactn, acematacin, fentiazac, clindanac, oxpinac, and fenclozic acid. Structurally related acetic acid derivatives having similar analgesic and antiinflammatory properties are also intended to be encompassed by this group.

Thus, "acetic acid derivatives" as defined herein are nonnarcotic analgesics/nonsteroidal antiinflammatory drugs having a free —$CH_2COOH$ group (which optionally can be in the form of a pharmaceutically acceptable salt group, e.g., —$CH_2COO^-Na^+$), typically attached directly to a ring system, preferably to an aromatic or heteroaromatic ring system.

The fenamic acid derivatives which may be used comprise: mefenamic acid, meclofenamic acid, flufenamic acid, niflumic acid, and tolfenamic acid. Structurally related fenamic acid derivatives having similar analgesic and anti-inflammatoryproperties are also intended to be encompassed by this group.

Thus, "fenamic acid derivatives" as defined herein are nonnarcotic analgesics/nonsteroidal antiinflammatory drugs which contain the basic structure:

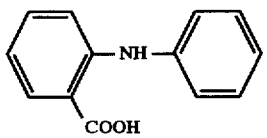

which can bear a variety of substituents and in which the free —COOH group can be in the form of a pharmaceutically acceptable salt group, e.g., —$COO^-Na^+$.

The biphenylcarboxylic acid derivatives which can be used comprise: diflunisal and flufenisal. Structurally related biphenylcarboxylic acid derivatives having similar analgesic and antiinflammatory properties are also intended to be encompassed by this group.

Thus, "biphenylcarboxylic acid derivatives" as defined herein are nonnarcotic analgesics/nonsteroidal antiinflammatory drugs which contain the basic structure:

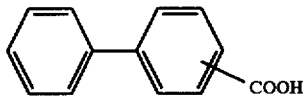

which can bear a variety of substituents and in which the free —COOH group can be in the form of a pharmaceutically acceptable salt group, e.g., —$COO^-Na^+$.

The oxicams which can be used in the present invention comprise: piroxicam, sudoxicam, isoxicam, and 4-hydroxy-1,2-benzothiazine 1,1-dioxide 4-(N-phenyl)-carboxamide. Structurally related oxicams having similar analgesic and antiinflammatory properties are also intended to be encompassed by this group.

Thus, "oxicams" as defined herein are nonnarcotic analgesics/nonsteroidal antiinflammatory drugs which have the general formula:

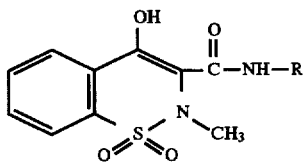

wherein R is an aryl or heteroaryl ring system.

The following NSAIDS may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclofenac, fenclorac, fendosal, fenfluminzole, fentiazac, feprazone, floctafenine, flunixin, flunoxaprofen, fluproquazone, fopirtoline, fosfosal, furcloprofen, furofenac, glucametacin, guaimesal, ibuproxan, isofezolac, isonixin, isoprofen, isoxepac, isoxicam, lefetamine HCl, leflunomide, lofemizole, lonazolac calcium, lotifazole, loxoprofen, lysin, clonixinate, meclofenamate sodium, meseclazone, microprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenaxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

Finally, NSAIDS which may also be used include the salicylates, especially aspirin, and the phenyl-butazones, and pharmaceutically acceptable salts thereof.

The compounds of Formula I may be prepared generally by the following processes described and illustrated in Schemes I and II.

The starting aldehydes of Formula 2 are known and can be prepared according to U.S. Pat. No. 4,981,865 which is incorporated herein by reference.

A general method for the preparation of a compound of Formula I is condensation of aldehyde 2 with a reagent of Formula 4 or 5. Phosphonium salts of Formula 4 where X=N-OMe are obtained from lactams 3 where X=N-OMe, prepared from α-bromo-γ-butyrolactones or α-bromo-δ-valerolactones. Phosphonium salts of Formula 4 where X=O, are prepared from α-bromo-γ-butyrolactones or α-bromo-δ-valerolactones of Structure 3 where X=O. Thus phosphonium salts are obtained by treatment of the halo compound with a tertiary phosphine, preferably triphenylphosphine, in a solvent such as toluene, or preferably tetrahydrofuran, at elevated temperatures. Phosphonium salts 4 are converted to the corresponding phosphoranes 5 by treatment with a strong base such as a metal hydride or alkyl lithium, in a solvent such as diethyl ether or tetrahydrofuran, or a metal alkoxide in an alcohol solvent. Alternatively a weak base such as sodium carbonate, in a solvent mixture of water and alcohol, or an organic base such as triethylamine in a solvent such as ethanol can be used. In the case of compounds where X=N-OMe, the phosphoranes are not isolated but are generated in situ and immediately reacted with a desired aldehyde of Formula 2 in a solvent such as ethanol at elevated temperatures. The isolated phosphorane derivatives are reacted with aldehydes of Formula 2 in a solvent such as toluene or dimethyl-sulfoxide at temperatures of 60°–80° C. to provide compounds of Formula 1, where Y=O.

Other reagents can also be combined with aldehydes of Formula 2 to provide compounds of Formula 1, where Y=O. Examples include the phosphonate derivatives of Formula 6 known as the Horner-Emmons or Wadsworth-Emmons modification (see March J, Advanced Organic Chemistry, 4th Edition, 959 (1992)). The phosphonate derivatives are obtained from the corresponding halo derivatives 3 by heating with a trialkyl phosphite. The phosphonates are converted to the corresponding ylids by treatment with a base preferably sodium hydride in a solvent such as toluene or 1,2-dimethoxyethane or with sodium amide in tetrahydrofuran at temperatures from 0°–65° C. and reacted with aldehydes of Formula 2 to provide compounds of Formula 1, where Y=O.

Trialkylsilane derivatives of Formula 7 are also known (for references on this modification known as the Peterson olefination reaction see March J, p 952). The lithium or magnesium salt of 7 is prepared with the corresponding base and is then added to the desired aldehyde 2 yielding a β-hydroxysilane, which eliminates water to give compounds of Formula 1, where Y=O.

Direct condensation of active methylene compounds of Formula 8 with aldehydes of Formula 2 would also provide the desired compounds. These reactions can be performed in the presence of a base such as a sodium alkoxide or preferably with a secondary amine such as piperidine in an alcoholic solvent (see March J, supra, p 945). A wide range of other bases and solvents can be employed.

SCHEME I

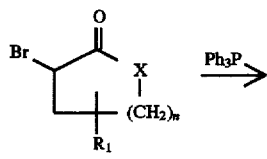

3
X = O, N-OMe
n = 1,2
$R_1$ = H, Me, Et

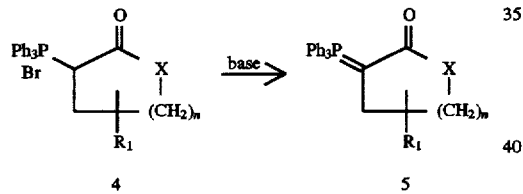

4      5

-continued
SCHEME I

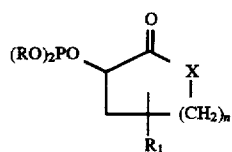

6

R = Me, Et

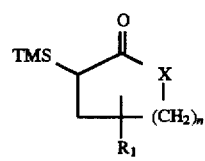

7

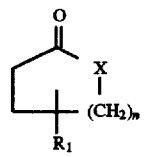

8

Scheme II depicts the condensation of reagents such as 4–8 with aldehydes of Structure 2. Thionation with $P_2S_5$ or preferably Lawesson's Reagent in a solvent such as toluene or THF provides I where Y=S (see Scheibye S, et al, *Tetrahedron* 35, 1339 (1979)).

SCHEME II

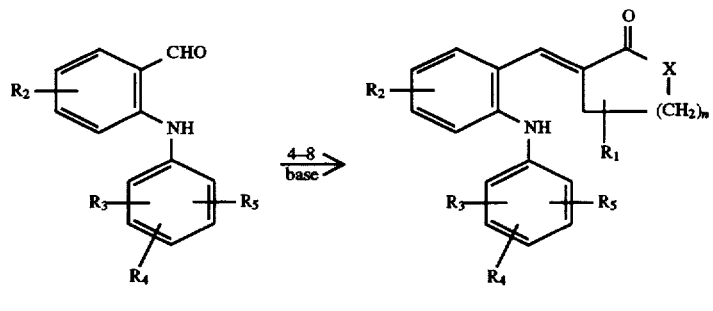

2                1; Y = O

Lawesson's Reagent or $P_2S_5$

-continued
SCHEME II

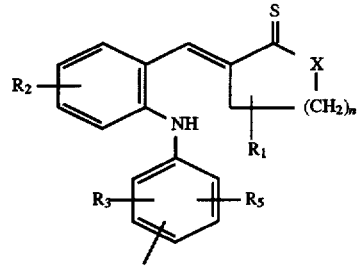

1; Y = S

The invention is further illustrated by the following representative examples. Such examples are not meant to be limiting.

EXAMPLE 1

(E)-3-[[2-[(2,6-Dichloro-3-methylphenyl)amino]phenyl]-methylene]4,5-dihydro-2(3H)-furanone To a room temperature solution of 2-[(2,6-di-chloro-3-methylphenyl)amino]benzaldehyde (915 mg, 3.26 mmol) in 40 mL of toluene is added triphenyl-phosphoranylidene-δ-butyrolactone (Fliszar S, Hudson R. F., Salvatori G, *Helv. Chim. Acta* 46, 1580 (1963)) (1.61 g, 4.65 mmol). The reaction mixture is heated at 70° C. for 1 hour. The solution is concentrated in vacuo and purified by flash chromatography eluting with hexane:ethyl acetate (3:1) to provide 1.01 g (89%) of (E)-3-[[2-[(2,6-dichloro-3-methylphenyl)amino]phenyl]methylene]-4,5-dihydro-2(3H)-furanone; mp=164°–164.5° C. dec.

Analysis calculated for $C_{18}H_{15}Cl_2NO_2$:
  C, 62.08; H, 4.34; Cl, 20.37; N, 4.02.
  Found: C, 62.21; H, 4.11; Cl, 20.19; N, 3.76.

EXAMPLE 2

(E)-3-[[2-[(2,6-Dichloro-3-methylphenyl)amino]phenyl]-methylene]-4,5-dihydro-2(3H)-furanthione A solution of (E)-3-[[2-[(2,6-dichloro-3-methyl-phenyl)amino]phenyl]methylene]-4,5-dihydro-2(3H)-furanone (386 mg, 1.11 mmol) and Lawesson's Reagent (273 mg, 0.68 mmol) in 15 mL of toluene is heated at reflux for 1.5 hours. The solution is concentrated in vacuo and purified by flash chromatography eluting with hexane:ethyl acetate (3:1) to provide 188 mg (47%) of (E)-3-[[2-[(2,6-dichloro-3-methylphenyl)amino]-phenyl]methylene]-4,5-dihydro-2 (3H)-furanthione; mp=163°–165° C. dec.

Analysis calculated for $C_{18}H_{15}Cl_2NOS$:
  C, 59.34; H, 4.15; Cl, 19.47; N, 3.85; S, 8.80.
  Found: C, 59.01; H, 4.11; Cl ,19.42; N, 3.64; S, 8.69.

EXAMPLE 3

(E)-4,5-Dihydro-3-[[2-[[3-(trifluoromethyl)phenyl]-amino]phenyl]methylene]-2(3H)-furanone To a room temperature solution of 2-[[3-(trifluoromethyl)phenyl]amino]benzaldehyde (327 mg, 1.23 mmol) in 14 mL of toluene is added triphenylphosphoranylidene-δ-butyrolactone(549 mg, 1.59 mmol). The reaction mixture is heated at 60° C. for 1.5 hours. The solution is concentrated in vacuo and purified by flash chromatography eluting with hexane:ethyl acetate (3:1 to 1:1) to provide 378 mg (92%) of (E)-4,5-dihydro-3-[[2-[[3-(trifluoromethyl)-phenyl]amino] methylene]-2(3H) furanone; mp=119°–120° C. dec.

Analysis calculated for $C_{18}H_{14}NO_2F_3$:
  C, 64.86; H, 4.23; N, 4.20.
  Found: C, 64.99; H, 4.31; N, 4.08.

EXAMPLE 4

(E)-4,5-Dihydro-3-[[2-(phenylamino)phenyl]methylene]-2(3H)-furanone

To a room temperature solution of 2-(phenylamino)-benzaldehyde (92 mg, 0.47 mmol) in 7 mL of toluene is added triphenylphosphoranylidene-5- butyrolactone (203 mg, 0.59 mmol). The reaction mixture is heated at 80° C. for 1.5 hours. The solution is concentrated in vacuo and purified by flash chromatography eluting with hexane:ethyl acetate (2:1) to provide 109 mg (89%) of (E)-4,5-dihydro-3-[[2-(phenylamino)phenyl]-methylene]-2(3H)-furanone; an analytical sample was obtained by recrystallization from hexane-ethyl acetate; mp=136.5°–137° C. dec.

Analysis calculated for $C_{17}H_{15}NO_2$:
  C, 76.96; H, 5.70; N, 5.28.
  Found: C, 76.57; H, 5.81; N, 4.98.

We claim:

1. A compound of the formula

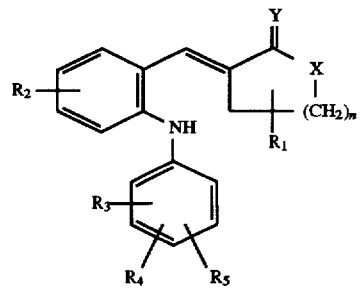

wherein
  X is O;
  Y is O or S;
  $R_1$ is hydrogen or lower alkyl;
  n is an integer of 2; and
  $R_2$, $R_3$, $R_4$ and $R_5$ are each independently hydrogen, halogen, trifluoromethyl, lower alkyl, CN, hydroxy, lower alkoxy, $S(O)_m$-lower alkyl, $NO_2$, or $NR_6R_7$ wherein $R_6$ and $R_7$ are each independently hydrogen, lower alkyl, lower alkanoyl or benzoyl, and m is an integer of 0, 1, or 2, or a pharmaceutically acceptable acid addition salt thereof.

2. A compound of claim 1 wherein Y is O.

3. A compound of claim 1 wherein Y is S.

4. A compound of claim 1 wherein $R_1$ is hydrogen, methyl, or ethyl.

5. An antiarthritic pharmaceutical composition comprising an antiarthritic effective amount of a compound of claim 1 and a pharmaceutically acceptable carrier.

6. A pharmaceutical composition for the treatment of a condition advantageously affected by the inhibition of IL-1 or other agonist-induced proteoglycan degradation which comprises an amount effective for the treatment of the condition of a compound of claim 1 together with a pharmaceutically acceptable carrier.

7. A method of treating arthritis in a mammal suffering therefrom which comprises administering to said mammal a pharmaceutical composition of claim 1.

* * * * *